United States Patent [19]

Scott

[11] Patent Number: 4,655,209

[45] Date of Patent: Apr. 7, 1987

[54] SURGICAL DRESSING AND PACKAGING

[76] Inventor: Douglas G. Scott, 677 Glancaster Road, Mount Hope, Ontario, Canada, L0R 1W0

[21] Appl. No.: 859,425

[22] Filed: May 5, 1986

[51] Int. Cl.⁴ ............................................. A61L 15/00
[52] U.S. Cl. .................................................... 128/156
[58] Field of Search ................................. 132/156, 155

[56] References Cited

U.S. PATENT DOCUMENTS

| 3,545,442 | 12/1970 | Wicker ................................ | 128/156 |
| 3,814,101 | 6/1974 | Kozak ................................. | 128/156 |
| 3,824,996 | 7/1974 | Carlisle .............................. | 128/156 |
| 3,903,882 | 9/1975 | Augurt ................................ | 128/156 |
| 3,927,669 | 12/1975 | Glatt .................................. | 128/156 |
| 4,094,316 | 6/1978 | Nathanson ........................ | 128/156 |

Primary Examiner—Gregory E. McNeill
Attorney, Agent, or Firm—Ridout & Maybee

[57] ABSTRACT

A compress type bandage differs from regular bandages of this type in that the bandage portion is formed of gauze having substantial longitudinal elasticity, sewn to opposite edges of a pad having two absorbent layers, at least one of which has sufficient tensile strength that tension from the bandage tails is transmitted through the pad material rather than the gauze. The multiple layers of the pad provide pockets useful for the application of medicaments, splinting and other uses, one pocket being subject to the bandage tension and the other being relatively uncompressed. In an alternative embodiment, at least the outer layer of the pad material is formed into a loop which is sewn to the gauze at a single location extending in both longitudinal directions against the gauze so that the loop can be folded upon itself to form a double thickness transverse pad.

9 Claims, 7 Drawing Figures

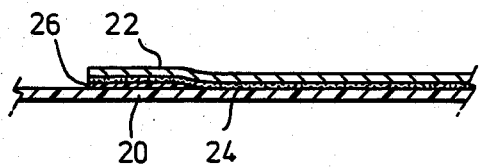
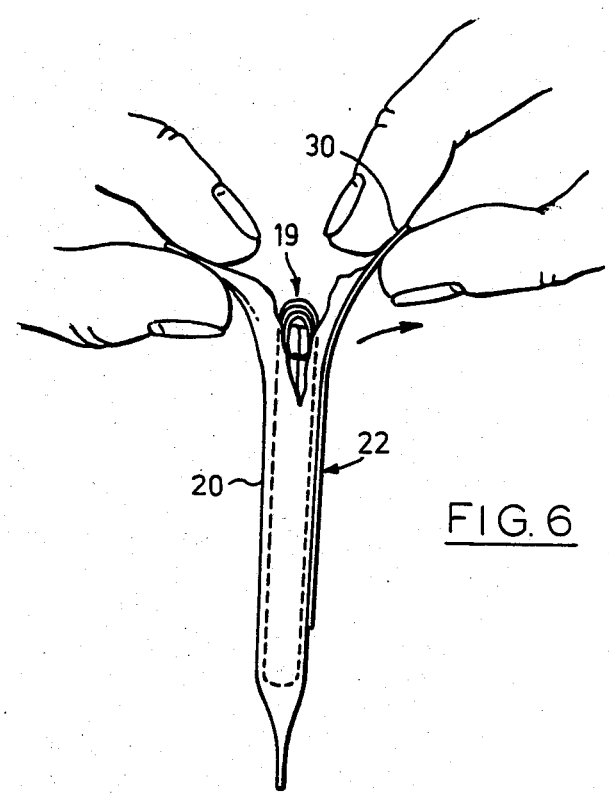
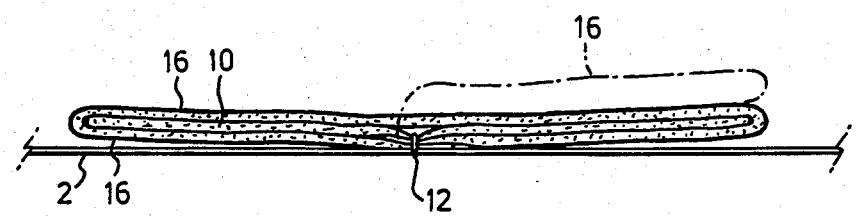

SURGICAL DRESSING AND PACKAGING

This invention relates to surgical bandages and packaging especially suited for such dressings, althoug having other potential applications. More specifically, the invention relates to compress type bandages comprising a dressing pad and gauze tails by means of which the pad may be held in place on a patient over a wound.

The traditional compress type bandage consists of a sterile absorbent pad, sewn or otherwise attached to a length of surgical gauze. It is simple, cheap and effective, but has some limitations. Care must be exercised in applying the gauze tails so as not to cause constrictions that may restrict blood flow. The bandage must normally be removed in order to apply medication to the wound, and since the pads tend to stick to wounds, removal of the bandage may break or pull away protective scabs. Whilst the bandages may be sealed in packages to protect sterility, it is often difficult to open such packages and unwrap the product for use without endangering the sterility of the pad, particularly when working under adverse conditions.

Objects of the present invention are to provide an improved compress type bandage which tackles these problems and is more versatile in operation, together with packaging which facilitates application of the bandage without endangering the sterility of the pad.

A compress type bandage in accordance with the invention comprises a length of surgical gauze, and a dressing pad formed of layers having opposite edge portions sewn to the gauze, wherein the gauze has substantial longitudinal elasticity, and the pad comprises at least two separable superposed absorbent layers, both layers comprising an absorbent padding. In one embodiment, at least one layer has high tensile strength and limited extensibility at least in the longitudinal direction, and the opposite edge portions of the pad are sewn to the gauze at longitudinally spaced locations such that the innermost part of the gauze lies parallel to the pad in substantially unextended condition. In a second embodiment, the pad comprises a loop of material sewn to the gauze at a single location so that the loop forms two layers of the pad, which may be folded upon itself.

Preferably the surface of the absorbent layer furthest from the gauze is laminated with a porous film of synthetic resin selected to minimize adherence to wounds, such as polyethylene.

Preferably the bandage is folded and sealed with a package comprising a polyethylene film envelope, having adhered to to an outer surface of one of its opposite sides, by means of a high tenacity adhesive, an underside surface of a label of soft polyvinyl chloride film having a tensile strength substantially greater than that of the polyethylene film, the side of the label adhered to the envelope having non-adherent marginal portions including one such portion of a width sufficient for easy finger grip located close to one marginal edge of the envelope, whereby upon gripping and pulling apart said one label marginal portion and said one envelope marginal portion, the label is tornout of the package to leave an aperture through which the contents may be removed. Preferably the underside surface of the label is fully coated with adhesive, and the non-adherent marginal portions are provided by application of an adhesive deadener to those portions.

FIG. 5 is a section through a portion of one side of the package of FIG. 4;

FIG. 6 is a side view illustrating the package of FIG. 4 in the course of being opened; and FIG. 7 is an edge view through the central portion of an alternative embodiment of bandage, showing in broken lines how the pad may be folded;

Figure 1:
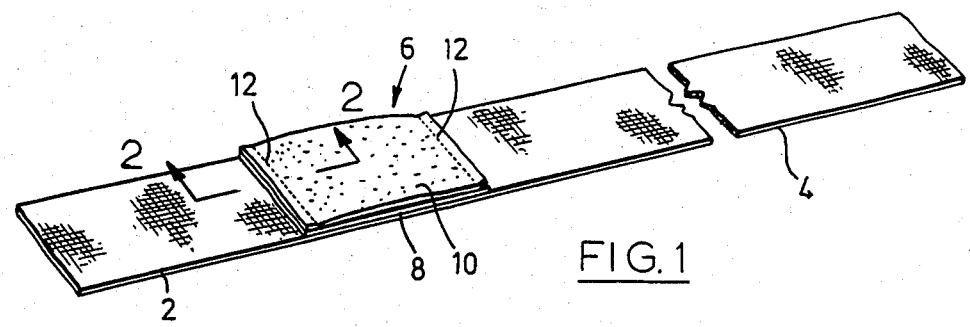
FIG. 1 is a perspective view of a bandage according to the invention, laid out flat.
Figure 2:
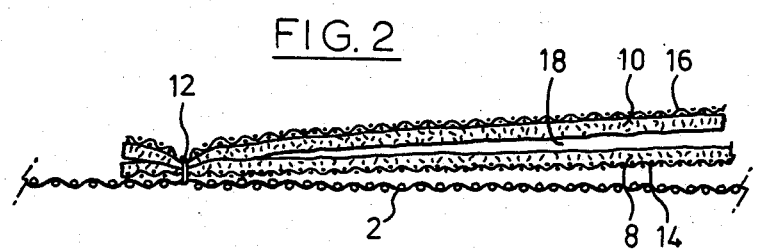
FIG. 2 is a diagrammatic longitudinal section through a central portion of the bandage of FIG. 1.
Figure 3:
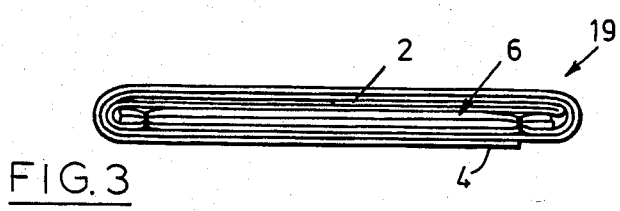
FIG. 3 is an end view of a bandage folded ready for packaging.

Referring to FIGS. 1 and 2, a compress bandage comprises a continuous strip of gauze sewn to a dressing pad 6 to form two tails 2 and 4 extending to either side of the pad. In the present instance, the gauze strip is provided with substantial longitudinal elasticity by forming the warp threads of material such as crimped nylon fibres. The pad is preferably offset from the centre of the strip so that the tail 4 is longer than the tail 2, so as to assist in application. The pad itself is formed by two distinct separate superposed layers of padding 8 and 10, sewn at opposite edges by stitching 12 to the gauze strip whilst the latter is in a substantially unstretched condition. The layer 8 of padding closest to the gauze is felt typically produced by needle punching polyester fibre through high tensile mesh 14 such as that sold under the trade mark REMAY. Such a layer has very limited extensibility and provides for the transfer of tensile forces between the tails 2 and 4 without stressing the portion of the gauze strip between the seams. At the same time the elasticity of the gauze tails 2 and 4 enables them to accommodate better to the figure of the patient without applying excess pressure to parts of a body or limb around which the tails are wrapped.

The layer 10 is formed by a felt, typically of rayon fibre, with a permeable non-stick external surface layer 16, typically of highly perforated polyethylene such as DELMET film from Hercules Inc.

The separate layers of padding form between them an inner pocket 18 into which medicaments or other materials may be inserted to treat a wound, in which additional absorbent padding may be inserted, or which may be used to hold splints or other devices. Likewise, the gauze between the seams and the layer 8 forms an outer pocket which may be similarly utilized. As compared with the other pocket, the inner pocket is subject to pressure from the tensioned layer 8 when the compress is in use, whilst the outer pocket is subject only to the pressure applied by the resiliency of the elastic gauze. Thus by choosing one or other of the pockets, a wide range of utility is available. The inner pocket can hold a splint or the like relatively firmly, whilst the outer pocket can hold a saturated absorbent pad without squeezing out its contents to an excessive degree; this outer pocket can moreover be readily utilized without releasing or loosening the bandage. In consequence, the bandage retains the functionality of the conventional compress bandage whilst providing a greatly extended range of utility with reduced risk of constricting normal blood flow due to excessive local pressure from the tails.

In the embodiment of bandage shown in FIG. 7, the materials and components utilized are similar, but instead of the edges of the layers forming the pad 6 being attached to the gauze by stitching 12 at longitudinally spaced locations, both edges of the layer are folded inwards and stitched to the gauze at the same location so as to form a loop. The layer 10, also stitched to the gauze at the same point, may be a single layer as above, or a further loop. If the pad is folded in half, as also shown in broken lines, a double thickness half width pad can be obtained, which still however presents the layer 16 to the wound. By suitable proportioning of the pad, it can be arranged that the pad has its long dimension extending longitudinally of the bandage when not folded, and laterally of the pad when folded.

It is obviously important that the sterility of such bandages be maintained until application, and for this reason such products are generally marketed in sterile packaging. It is also important, since such bandages may often need to be used in the field under adverse conditions, that it is possible easily to remove a bandage from its sterile packaging and apply it to a patient without unduly prejudicing sterility of at least the wound contacting parts of the bandage, particularly the pad.

Figure 4:
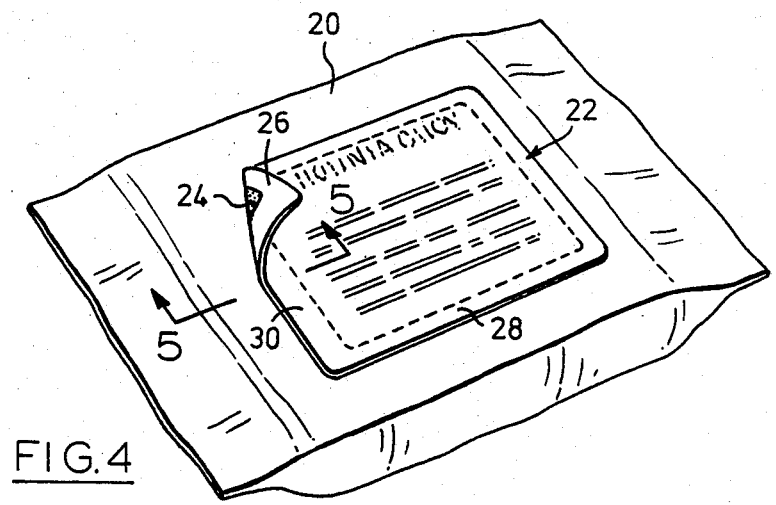
FIG. 4 is a perspective view of a packaged bandage.

I have developed a package especially adapted for the above described bandage but also suitable for other products, which is capable of maintaining sterility prior to opening, yet is easily opened to permit removal of the bandage and its deployment for use. The package shown in FIGS. 4 and 6 is based on a plastic film envelope 20, typically of polyethylene, within which the bandage, suitably folded, can readily be sealed utilizing conventional heat sealing equipment. The bandage is preferably folded by forming multiple folds in the tail 4 so that it forms a pad overlaying the compress pad and wrapping the tail 2 around the pads so formed to provide a package 19. The tail 4 may either be placed against the film 16, or in the case of larger pads, the latter may be folded so as to protect the film 16.

In order to assist opening of the package, a special form of label is applied to the latter. The label 22 which identifies the product is printed on a flexible plastic film much stronger than the film of the package, typically soft polyvinyl chloride. The rear surface of the label carries a layer 24 of super-aggressive self curing adhesive having a very high adherence both to polyethylene and to polyvinyl (or to any alternative film materials that may be used). A suitable adhesive is that designated RG8-680V manufactured by Morgan Adhesives and sold under the trade mark MACTAC. Edge portions of the free surface of this adhesive layer are treated with an adhesive layer 26 so that edge portions 28, 30 of the label will not adhere to the film of the envelope 20. The abhesive layer may be of adhesive deadening flat varnish. This layer not only avoids the unwanted migration of adhesive from between the label and the envelope, which might cause unwanted stickiness and mutual adherence of envelope packages together, but also in the case of the wider edge portion 30 provides a nonadherent tab which may be gripped together with an adjacent edge of the envelope as seen in FIG. 6, and ripped away from the envelope. The high tenacity of the adhesive causes the film of the envelope beneath the label to be ripped away from the remainder, forming an opening through which the package 18 may be readily removed and then unfolded for use.

I claim:

1. A compress type bandage comprising a length of surgical gauze, and a dressing pad sewn to the gauze by lines of stitching at longitudinally spaced locations intermediate the ends of the length of gauze so that the end portions of the length of gauze form tails by means of tension in which the pad may be pressed against a wound, wherein the gauze has substantial longitudinal elasticity, and is sewn to the pad whilst in a substantially unextended condition, and the pad consists of at least two superposed absorbent layers readily separable from one another between the lines of stitching to form a pouch, both layers comprising absorbent padding, and at least one layer having high tensile strength and limited extensibility at least in the longitudinal direction.

2. A compress type bandage according to claim 1, wherein said one of the absorbent layers having high tensile strength comprises fibres needle punched through a high tensile webbing.

3. A compress type bandage according to claim 2, wherein said one layer is the layer nearest the gauze.

4. A compress type bandage according to claim 1, wherein the external surface of the absorbent layer furthest from the gauze is laminated with a porous film of synthetic resin selected to minimize adherence to wounds, such as polyethylene.

5. A compress type bandage comprising a length of surgical gauze having substantial longitudinal elasticity, and a dressing pad comprising a loop of absorbent padding material sewn to the gauze by a single line of transverse stitching intermediate the ends of the length of gauze so that the end portions of the gauze form tails by means of tension in which the pad may be pressed against a wound, the loop forming at least two superposed absorbent layers in the pad, readily separable from one another to form a pouch.

6. A bandage according to claim 5, wherein the loop can be folded upon itself at the location at which it is sewn to the gauze to double its thickness and halve its size.

7. A bandage according to claim 6, wherein the proportions of the loop are such that when unfolded its longitudinal axis extends parallel to the gauze, and when folded its longitudinal axis runs transverse to the gauze.

8. A compress type bandage folded and sealed within a package comprising a polyethylene film envelope, having adhered to one of its opposite sides by means of a high tenacity adhesive, an underside surface of a label of soft polyvinyl chloride film having a tensile strength substantially greater than that of the polyethylene film, the side of the label adhered to the envelop having nonadherent marginal portions including one such portion of a width sufficient for easy finger grip located close to one marginal edge of the envelope, whereby upon gripping and pulling apart said one label marginal portion and said one envelope marginal portion, the label is torn out of the package to leave an aperture through which the contents may be removed.

9. A compress type bandage according to claim 8, wherein the underside surface of the label is fully coated with adhesive, and the non-adherent marginal portions are provided by application of an abherent layer over the adhesive coating of those portions.

* * * * *